United States Patent
Bridges et al.

(10) Patent No.: US 9,817,950 B2
(45) Date of Patent: Nov. 14, 2017

(54) METHODS FOR SECURELY PROCESSING NON-PUBLIC, PERSONAL HEALTH INFORMATION HAVING HANDWRITTEN DATA

(71) Applicant: PaperClip Inc., Hackensack, NJ (US)

(72) Inventors: David Michael Bridges, Toms River, NJ (US); Michael Alexander Suleski, Warwick, NY (US)

(73) Assignee: Paperclip Inc., Hackensack, NJ (US)

( * ) Notice: Subject to any disclaimer, the term of this patent is extended or adjusted under 35 U.S.C. 154(b) by 0 days.

(21) Appl. No.: 14/682,747

(22) Filed: Apr. 9, 2015

(65) Prior Publication Data
US 2017/0076070 A1    Mar. 16, 2017

(51) Int. Cl.
| | |
|---|---|
| *G06K 9/00* | (2006.01) |
| *G06F 19/00* | (2011.01) |
| *G06Q 10/06* | (2012.01) |
| *G06F 21/62* | (2013.01) |
| *G06F 3/0488* | (2013.01) |
| *G06F 17/24* | (2006.01) |

(52) U.S. Cl.
CPC ........ *G06F 19/363* (2013.01); *G06F 3/04883* (2013.01); *G06F 17/248* (2013.01); *G06F 21/6245* (2013.01); *G06K 9/00442* (2013.01); *G06Q 10/06* (2013.01)

(58) Field of Classification Search
CPC .. G06F 17/248; G06F 19/363; G06F 21/6245; G06F 3/04883; G06K 9/00442; G06Q 10/06
See application file for complete search history.

(56) References Cited

U.S. PATENT DOCUMENTS

| | | | |
|---|---|---|---|
| 5,832,100 A | 11/1998 | Lawton et al. | |
| 6,043,819 A | 3/2000 | LeBrun et al. | |
| 2002/0194213 A1* | 12/2002 | Takayanagi | G06F 21/562 715/256 |
| 2005/0036681 A1 | 2/2005 | Lenoir | |
| 2008/0155540 A1 | 6/2008 | Mock et al. | |
| 2011/0078570 A1* | 3/2011 | Larsen | G06F 19/322 715/710 |
| 2014/0297346 A1 | 10/2014 | Mock et al. | |
| 2016/0171298 A1* | 6/2016 | Takeda | G06K 9/00469 382/176 |
| 2016/0171513 A1* | 6/2016 | Takeda | H04L 67/1002 705/7.29 |

OTHER PUBLICATIONS

International Search Report dated May 23, 2016 from corresponding International Application No. PCT/US2016/021479, 3 pages.
Written Opinion dated May 23, 2016 from corresponding International Application No. PCT/US2016/021479, 19 pages.

\* cited by examiner

*Primary Examiner* — Li Liu
(74) *Attorney, Agent, or Firm* — Ohlandt, Greeley, Ruggiero & Perle, L.L.P.

(57) ABSTRACT

The present method provides for conversion of handwritten to data that is accurate and fast, yet with improved security. The method provides handwritten data split into two or more components and, thus, provided, out of context, for conversion into printed data, and for the secured transmittal of printed data for assembly into context for transmission to the client. The present disclosure also provides for storage of the unassembled data for future use.

19 Claims, 16 Drawing Sheets

*Clean Form*

*Template – Areas of Interest Traced*

*Form Page Template*

FIG. 5

Snip-It Identification (Example)
Transaction# 1001
Form ID 1143
Form/Page ID 1
Data Dictionary LBTC
Data Dictionary Term P10-First Name
Special Data No
Split Factor 0
Mask XXXXXXXXXXXXXXXXXXX
Coordinates/Location X0.63Y1.63-X3.63Y2.25
Date Time Stamp 0212201514 2210

*Fig. 14B*

METHODS FOR SECURELY PROCESSING NON-PUBLIC, PERSONAL HEALTH INFORMATION HAVING HANDWRITTEN DATA

BACKGROUND OF THE DISCLOSURE

1. Field of the Disclosure

The present disclosure relates to methods for processing non-public, personal health information having handwritten data. More particularly, the present disclosure relates to methods for processing of collection of forms and data of non-public personal health information having handwritten data in order to submit only "In Good Order" (I-GO) data to the transaction company. Still more particularly, the present disclosure relates to such methods in which the handwritten data is processed out of context to assure security and at a completion stage placed into context for dissemination to the client or customer.

2. Description of the Related Art

In the 2000s, the goal was to not create paper, but instead use e-signed electronic documents. However, hand written forms remain the major transaction media in the financial services industry. Data methods drive the top line growth of business. However, the problem is that this data rests in handwriting on paper or scanned images.

The transformation of handwriting on paper to usable data by present technology has not been achieved. Today, companies hire off-shore organizations in order to leverage their inexpensive labor pool providing twenty-four (24) hour turnaround time. A second problem is that non-public information (NPI) and personal health information (PHI) pose a growing liability and cost to the financial services industry. The industry does not want to accept incomplete information that ultimately produces a Not In Good Order (NI-GO) transaction. NI-GO data and documents have to be retained and managed, as required by many laws and regulations, over extended periods of time by the receiving company. Thus, NPI/PHI offers no return on investment and only liability and risk for both the individuals and the receiving organizations. Still further, there is a problem of deriving complete I-GO information that has been processed in a secured methodology or manner throughout the process.

SUMMARY OF THE DISCLOSURE

The present disclosure provides a method for the most accurate, fastest turnaround time, fully compliant and least expensive handwriting to data conversion solution heretofore known.

The present disclosure also provides such a method in which handwritten data is split into components or Snip-Its and provided, out of context, to operators to assure security during processing of the handwritten data into printed data and the transmittal of printed data for assembly.

The present disclosure further provides such a method in which the printed data is assembled into context for transmission to the client or customer, yet is stored elsewhere in an unassembled, and thus out of context state.

The present disclosure still further provides such a method for the collection of forms and data that are deemed in good order while eliminating forms and data that are deemed not in good order before submission to the transaction company and all such data is secured during the entire processing and storage thereof.

The present disclosure also provides such a method that includes the steps of creation of a template based on handwritten data fields in a form that is selected based on a transaction company business requirements, and mapped to a data dictionary library that defines industry standards of the business of the transaction company to assure all information requirements for the form are met. The template identifies fields of data and the precise coordinates of the position of each data bit of data that has handwritten data and the criticality of the data bit; and sending, based on the template, selected data bits called Snip-Its to a plurality of data operators to determine the handwritten data bits and provide a print form of same within seconds of receipt by the data operator.

The present disclosure further provides such a method that can also include the steps of the selected assembly of the data bits into context for distribution of documents and data to a client or customer.

The present disclosure still further provides for the storage of the data bits in an out of context format to provide security and a series of identifiers on the data bits that can only be assembled or placed into context with appropriate instructional information.

The present disclosure yet further provides that the storage of the data bits in silos in a selected warehouse so that no one can determine any personal information until the information is compiled or placed into context even if unauthorized access to the warehouse occurs.

BRIEF DESCRIPTION OF THE DRAWINGS

FIG. 5 illustrates the step of the creation of a Form Page Template in accordance with the present disclosure.

FIGS. 14A to 14D show a Snip-It and a Snip-It assembled in accordance with the present disclosure. (Hereinafter, FIGS. 14A-14D are referred to collectively as FIG. 14).

DESCRIPTION OF EXEMPLARY EMBODIMENTS

Figure 1:
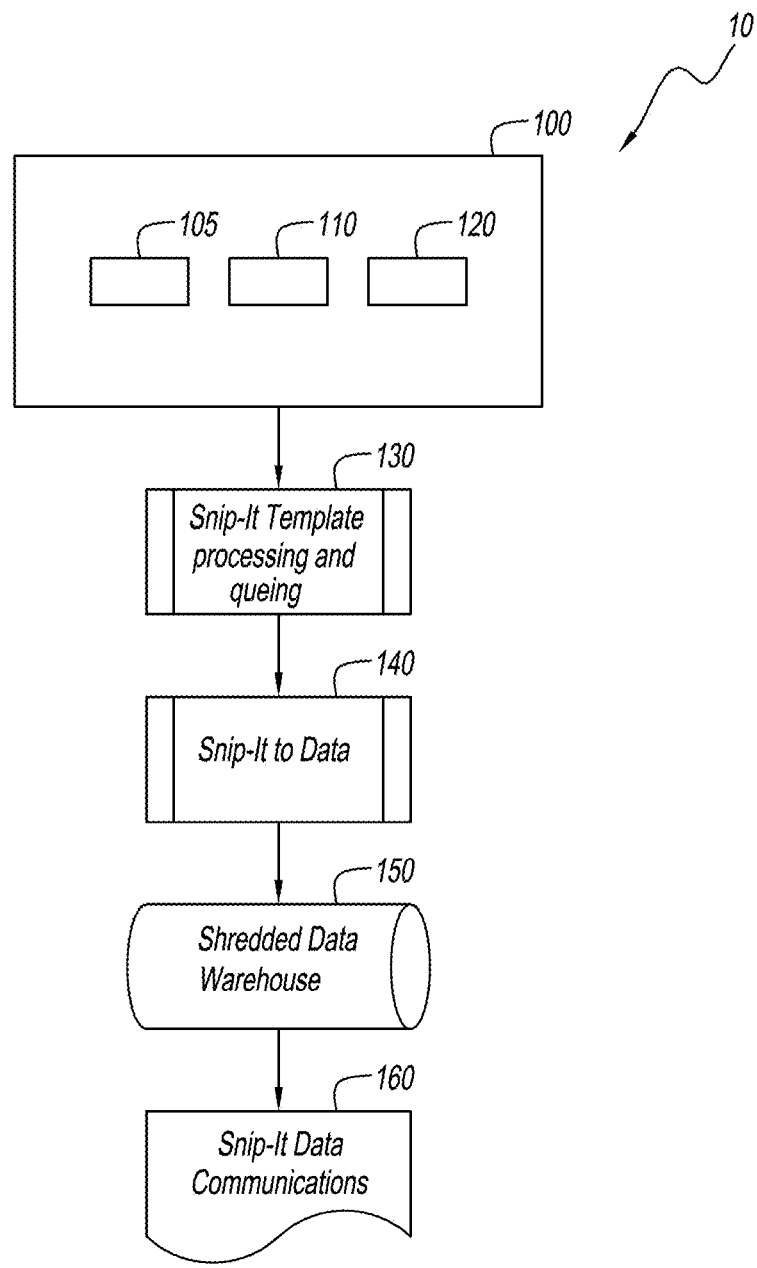
FIG. 1 is a flow diagram of the overall method of the present disclosure.

Referring to the drawings and, in particular, FIG. 1, the overall method of the present disclosure is generally represented by reference numeral 10. Method 10 has a number of steps. The first step, at 100, is the collection of initial transaction form images. The receipt of transaction form pages in total are assigned a transaction ID. At 105, each page, called an image form, of a form or document is received and provided with a unique identifier, such as, for example, a bate stamp number. Then, the image form is archived at 110. At 120, a form recognition step is used to completely identify the document, as well as the image form. This form recognition step uses bit map pattern analysis and programmatically matches the unidentified pages of a document to the pre-configured form of the transaction company that has been stored in a library, called a Fingerprint Library, discussed below. Preferably, there is a form recognition QA as an aspect of the present disclosure. This form recognition, and the form recognition QA, 120 are unique from current processes because the form recognition step 120 uses a different method to absolutely identify a form page.

The present method 10 also includes step 130 of the creation of a Snip-It Form Page Template, discussed in detail below, and the processing of the Snip-It, and the determination of the Snip-It to data at 140 which is the conversion of the handwritten data into printed data. Once converted, the Snip-It is sent to the Shredded Data Warehouse 150, and subsequently the Snip-It can be compiled or assembled into context for data communication at 160.

Figure 7A:
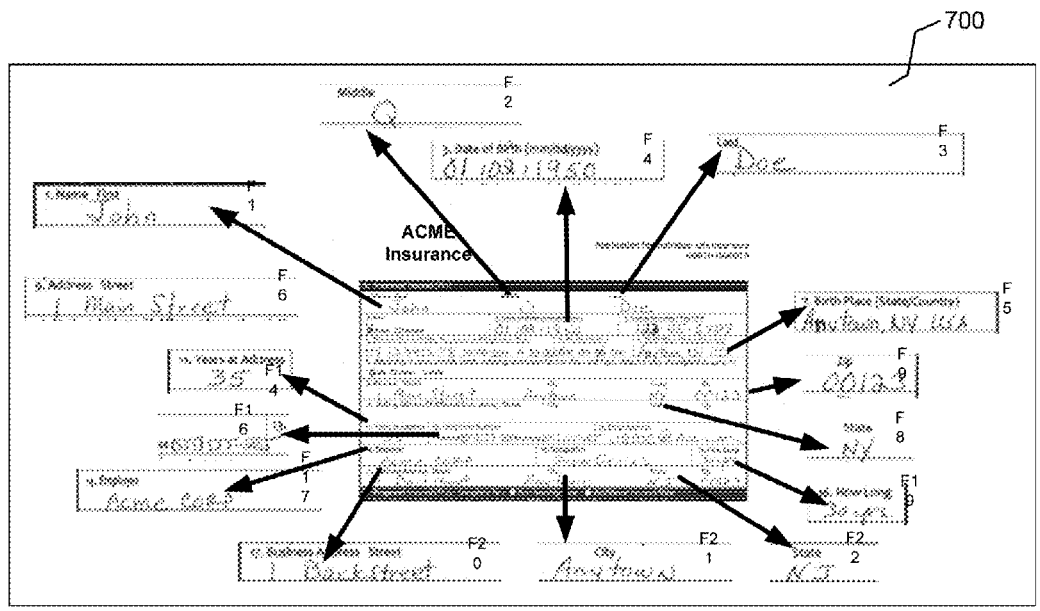
FIGS. 7A and 7B illustrate individual image areas to be extracted.

Snip-It as defined herein means a small image areas from a page with handwritten information, such as, for example, the last name of a person, address, phone number, social security number, and the like, that represent data elements. A typical Snip-It is shown in FIG. 7A and B.

A person or entity, such as a data entry person, called hereinafter a Sniper, receives one Snip-It at a time and enters into a browser the handwritten word(s) displayed in the received Snip-It. Thereafter, the Sniper moves to the next Snip-It received.

Figure 4:
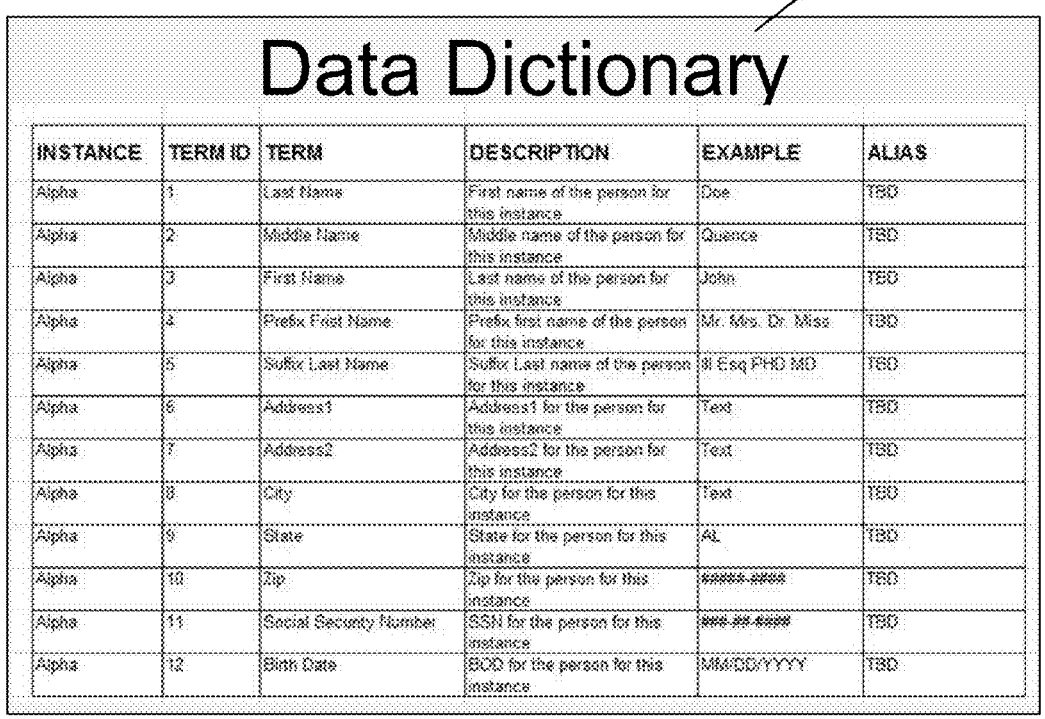
FIG. 4 illustrates a Data Dictionary for use in the present disclosure.

As used herein, a Data Dictionary is a compilation of terms and is a databank of all industry defined terms for all industries' standards organizations that may participate in the methods of the present disclosure. A Data Dictionary 400 is shown in FIG. 4 and a selected one in FIG. 14A.

Figure 11:
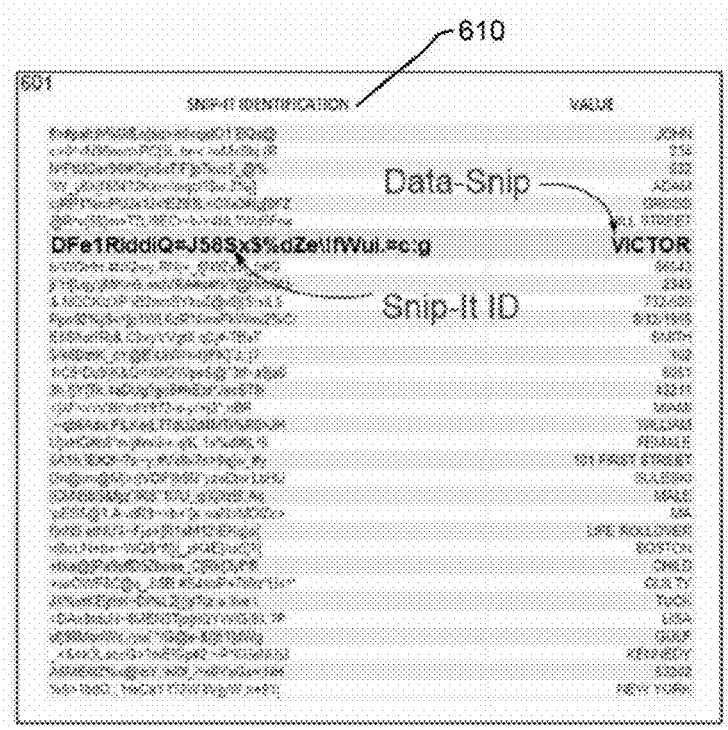
FIG. 11 is a schematic of a data silo in accordance with the present disclosure.

Data Snip-It is the transcribed digital or printed data derived from a Snip-It. Data Snip-It exists in a paired value (e.g., Snip-IT ID and Data Snip-It Value) is shown in FIG. 11.

A Fingerprint Library is a collection of form pages representing a form or form document. This Fingerprint Library allows for programmatic identification of submitted handwritten transaction form pages to be identified as uniquely identified or candidates for a Form Rec Sniper.

As used herein, image pattern recognition technology or application is used to capture unique patterns and catalog the results of the capture (e.g., fingerprints) for future programmatic comparisons or recognition. Two applications of this image pattern recognition application results in Clean Form Page 200 shown in FIG. 2 and Transaction Forms Page 260 shown in FIG. 3.

Figure 2:
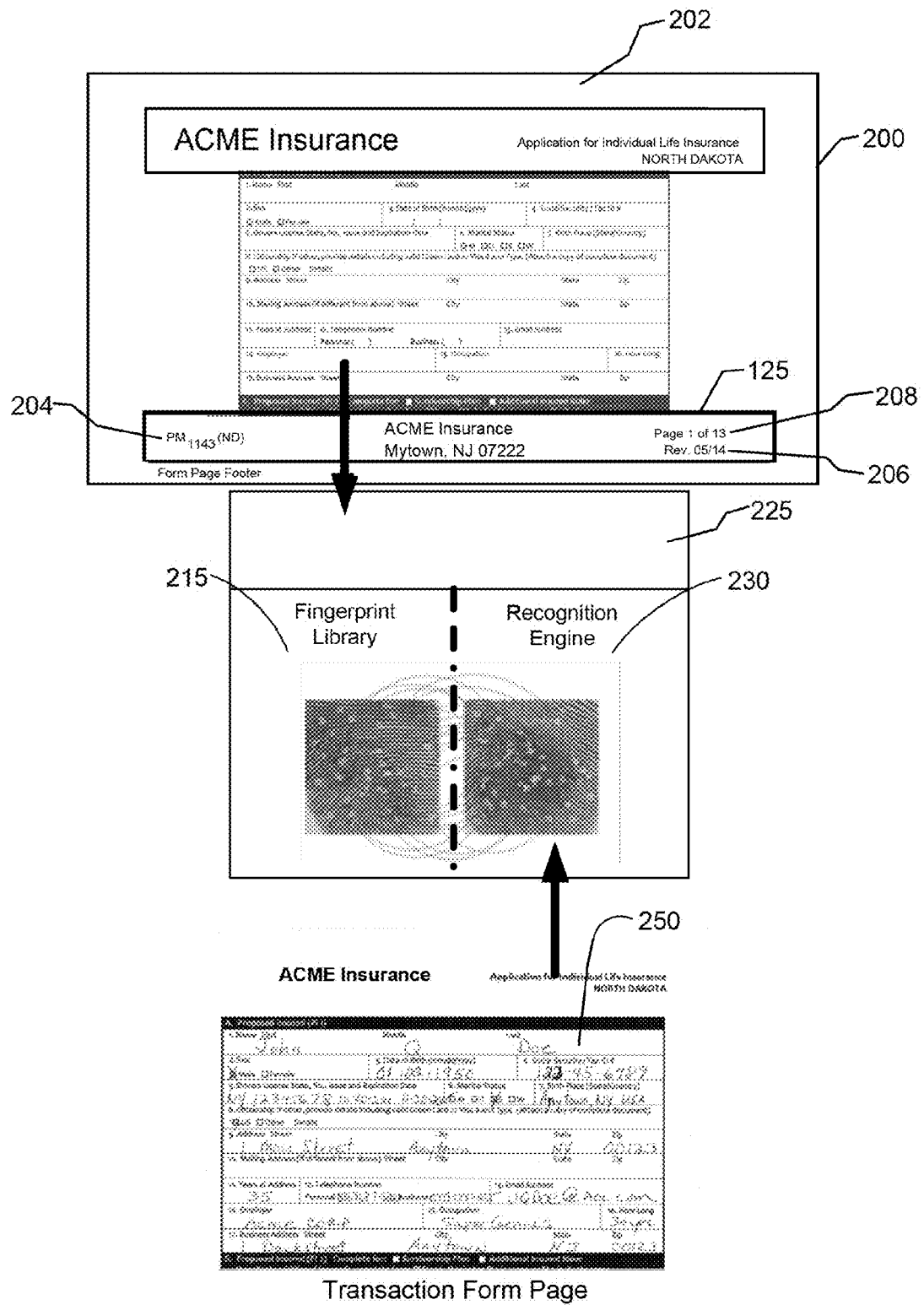
FIGS. 2 and 3 illustrate the recognition and storage of a Clean Form Page from a Transaction Form Page.

Referring to the form image collection step 100, when an image form or form 200 shown in FIG. 2 is initially received, form 200 is then entered, preferably using the image recognition application, into an established Fingerprint Library of archived forms 215. This Fingerprint Library 215 already has a number of forms for various business types exclusive to a transaction company, client or customer. This form image collection step 100 captures the original source and stores any metadata associated with image form 200 that identifies the transaction company.

Figure 3:
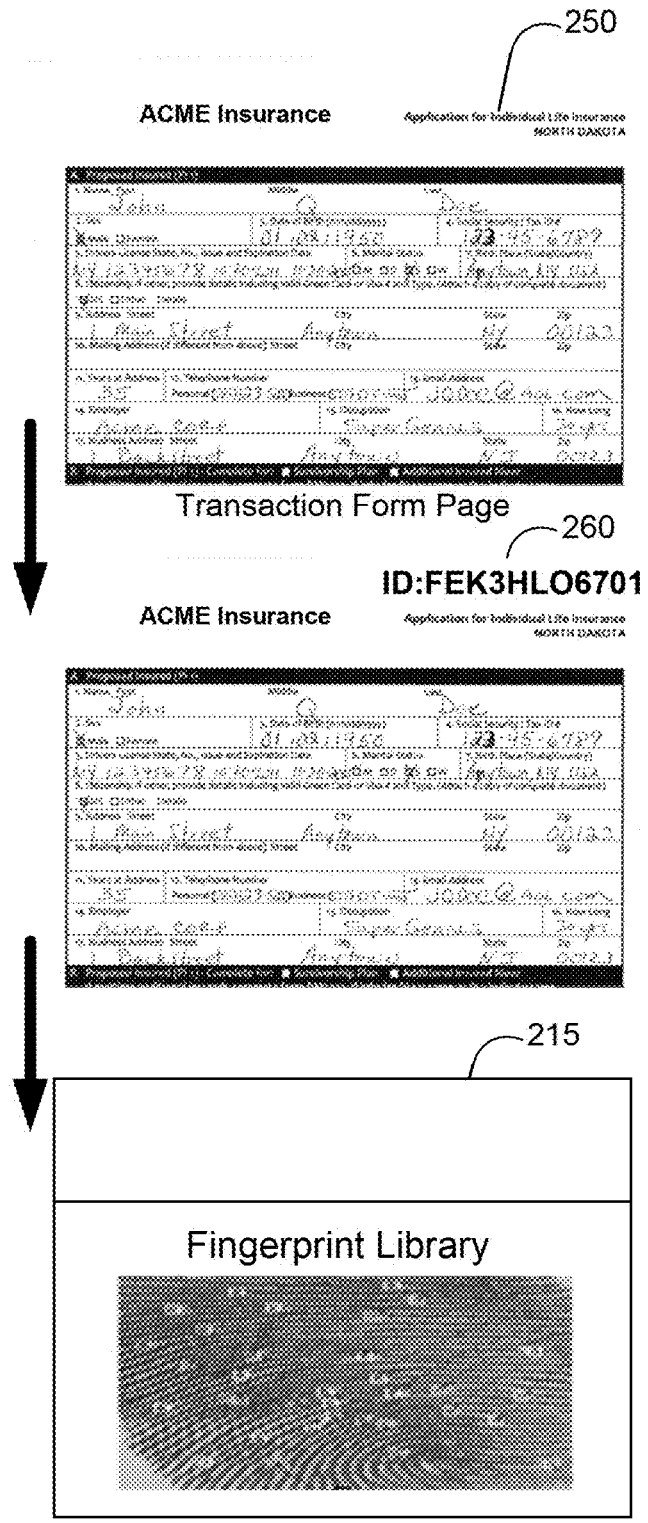

Once established, image form 200 receives its unique identifier, such as a bates stamp number at 110 shown in FIG. 1. Thus, image form 200 is then protected throughout the process. The bates stamp or unique identifier is used as the Snip-It location or identification of its location. Once integrity is established by the recognition engine 230, the form is documented by a process of fingerprinting and into the Fingerprint Library 215 shown in FIG. 2. As shown in FIG. 3, once the Transaction Form Page 260 is completed, it is also stored into Fingerprint Library 215. Specifically, each image form or page of a document is subjected to bit map pattern analysis. The fingerprint is archived based on a specific retention schedule selected by the customer. This bit map pattern assures that the integrity of the imaged form is established.

The Transaction Form Page 250 having handwritten data can be entered by conventional means, such as, for example, scanning or again using recognition technology, such as pattern recognition, to determine whether the form is already a form of the client in the library of forms. Specifically, as shown in FIG. 3, when the Transaction Form Page 250 arrives, metadata 260 describing the form will determine the form owner or source/transaction company at a minimum. Additional metadata, such as the sender, the transactional company, case number, policy number, document type, can be used to further narrow the scope of processing. With the source (i.e. ACME Insurance, DoE, New Jersey Driver License Dept., and the like) identified, the methods of the present disclosure, based on prior setup template configuration, what recognition method to use, namely CS Form Rec or recognition application.

Referring again to FIG. 2, once the Clean Form Page 200 is submitted to pattern recognition for fingerprinting, the many fingerprints for a given transaction company are organized in the Fingerprint Library at 215. A transaction company library can be the fingerprint Library 215 and is initially used to programmatically identify the form page. The process at 225 selects the number of form pages that are candidates for the correct Form Page. If more than one Form Page is produce, then a special operator, such as a FR Sniper, can determine the correct Form Page. At this time, the originality of the form and a chain of custody of the form in the process have now been established.

Figure 14A:
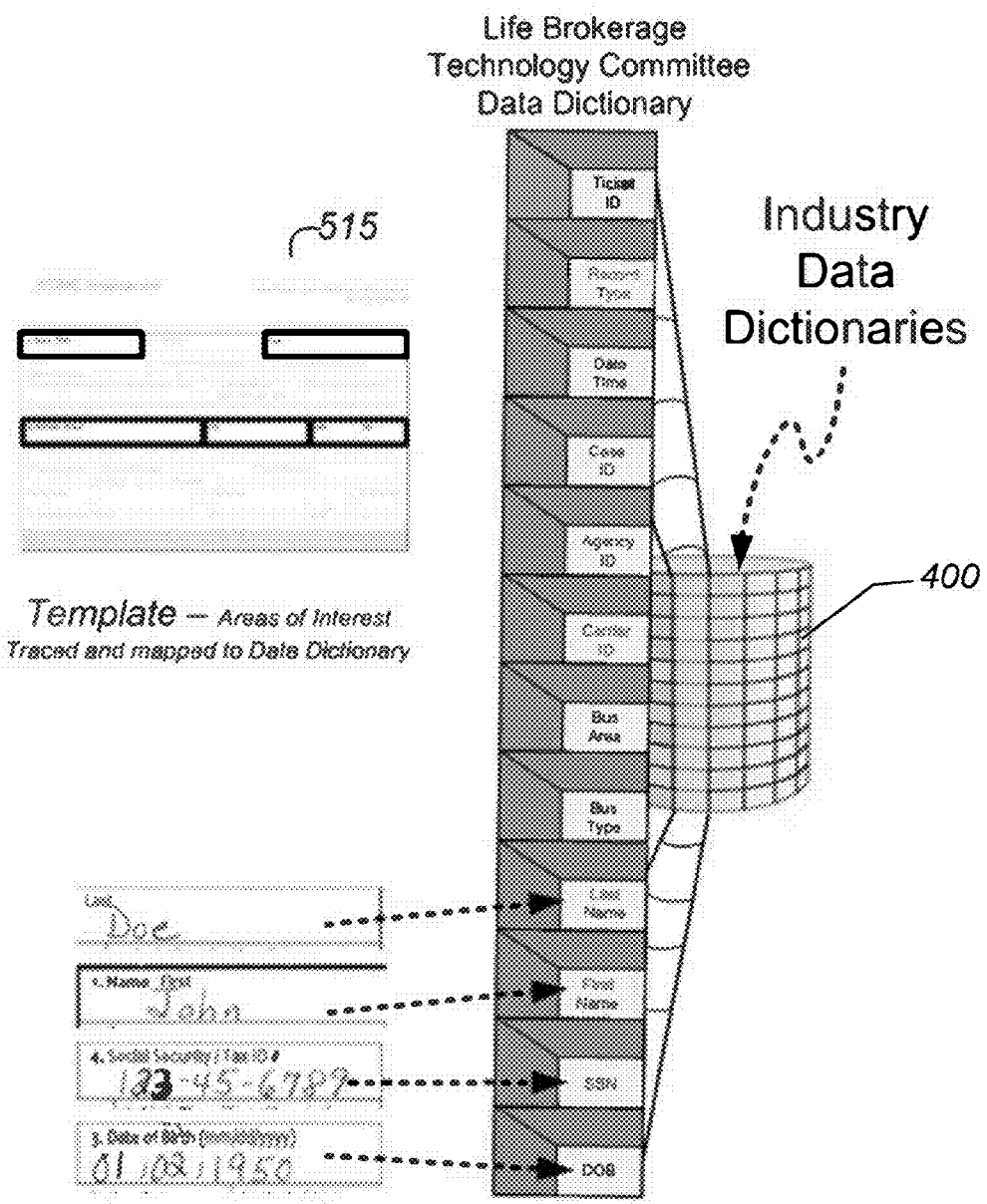

Hosting the Data Dictionary 400 of FIG. 4 provides a consistent mapping and eliminates term variation and non-standard characteristics. Transaction companies adhere to industry standards organizations (i.e., LBTC for life insurance, ACORD for P&C insurance, MISMO for mortgages, IRI for annuities). Data dictionary is a compilation of standard organization terms and custom transaction company terms. Every Snip-It receives a unique dictionary term association as shown, for example, in FIG. 14A. Referring to FIG. 14A, the Data Dictionary for Life Brokerage Technology Committee (LBTC) (a life insurance association) has certain required data to complete its forms, for example as shown, form ID, namely ticket ID, record type, date and time, case ID, agency ID, carrier ID, and bus area. Such data also includes the customer or client identifying information that is normally the handwritten data subject to the process of the present disclosure, namely a client's last name, first name, social security number and date of birth. These relationships to the Data Dictionary are defined in the Form Page Template 520 of FIG. 5. These relationships are factored into the creation of the Form Page Template 520, as well as the reassembly of Snip-Its into context at the end of the process of the present disclosure.

Forms processing according to the present disclosure is divided into two functions. One function is form recognition step 120. The other function is Snip-It recognition that is an important aspect of the present disclosure. For form recognition setup 120, the clean form is processed through fingerprinting and stored in a library of fingerprints shown as 200 in FIG. 2, will initially be processed to determine the company 202, form Id 204, version 206 and page number 208. This data will be tagged to the page, and identify the Snip-It Template.

It should be noted that the form recognition step 120 uses pattern recognition, not OCR, and also uses data entry operators or Snipers with no access to NPI or PHI information, which is known processes in which data entry operator have full access to NPI and PHI. Since current processes convert the bit map to data (OCR/ICR) recognizing the data to identify the form page. The current conventional process is less than accurate than that of the present disclosure since the operation has no control over image quality. Also, the current conventional process has found that third party scanning and capture solutions offer no consistency. Therefore, miss identified form pages have resulted in unauthorized NPI or PHI access. Accordingly, the present form recognition overcomes these problems of the current conventional process.

Figure 5:
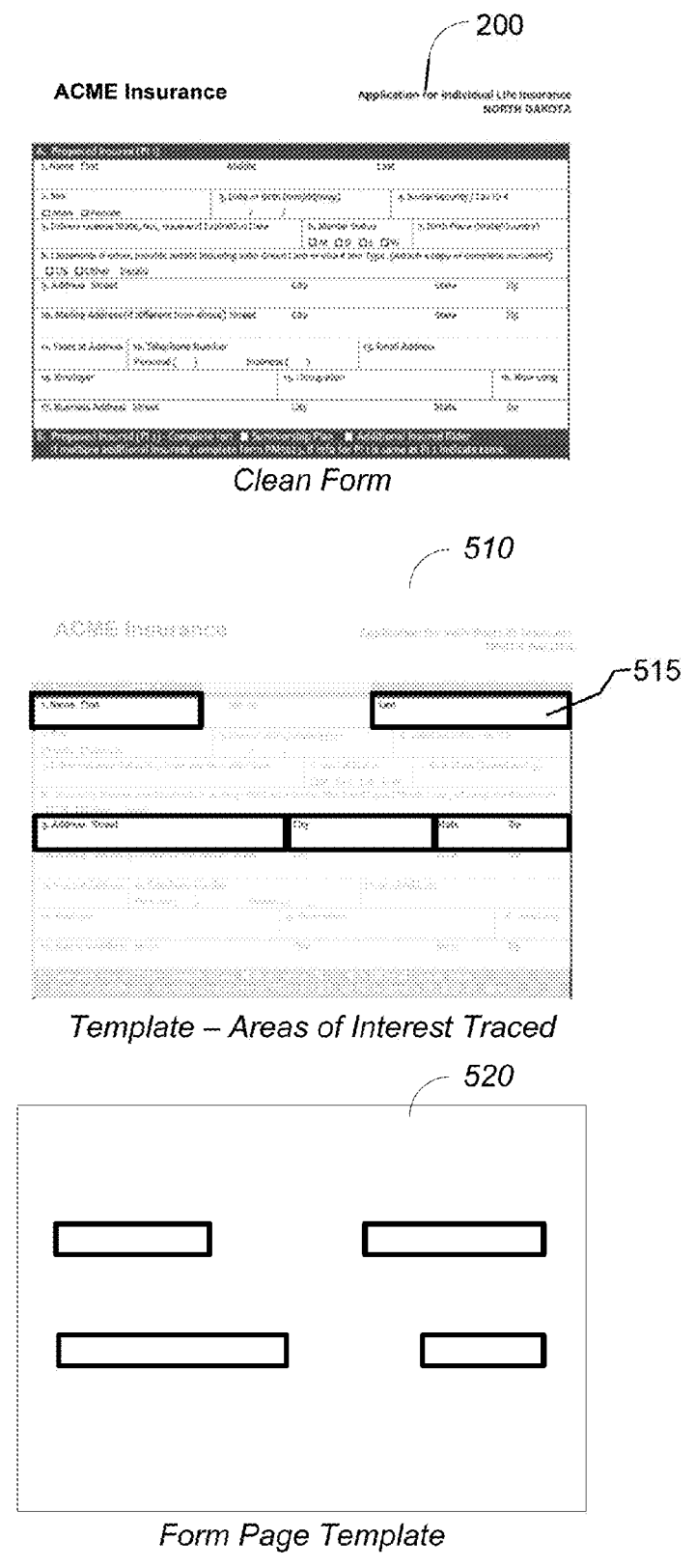

The next step in FIG. 1 is the creation 130 of Snip-Its from its Form Page Template 520 of FIG. 5. Referring to FIG. 5, the transaction company or customer first decides what, in Transaction Form Page 125 shown in FIG. 6, is handwritten data or information is critical for inclusion into Form Page Template 520.

Figure 7B:
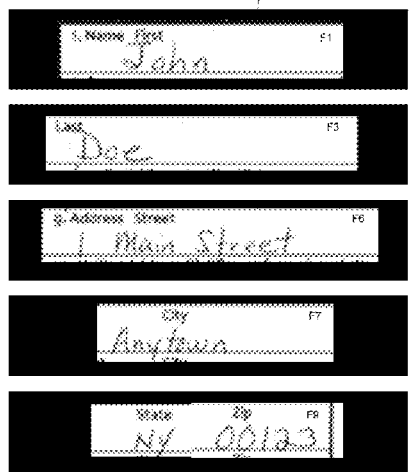
Figure 7C:
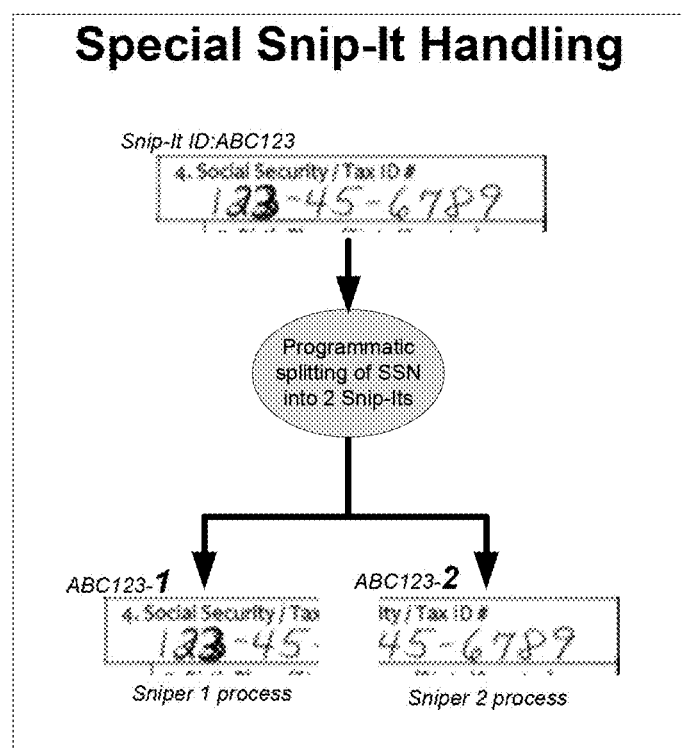
FIG. 7C illustrates a special Snip-It Handling. (Hereinafter, FIGS. 7A-7C are referred to collectively as FIG. 7).

Critical data or security data is defined as data that is secret or confidential information. It is data that can identify a person whose non-public or personal health information is being reviewed. Security data includes, but is not be limited to, social security number, driver license number, date of birth, credit card number and information, and the like information. Such Security data is shown in FIGS. 7A and 7B, and include, but is not limited to, the handwritten data, namely last name, first name, social security number, date of birth, address, employer and years of employment. Such security data will always be sub-divided into multiple Snip-Its, as shown in FIG. 7C, where there will be at least two data entry operator or Snipers so that no one Sniper will not have access to the entire Snip-It, i.e. will not have access to the complete image field. In fact, during the Snip-It process steps, discussed later herein, such security or critical data in one field of the form will be segmented within the field or created Snip-It so that the entire critical data in the field is never reviewed at once, and preferably by no one person, so that it will be impossible to determine from the Snip-It the entire security or critical data in the field. Further, each Snip-It will, preferably, have accuracy levels pre-defined based on whether the data is critical data or not. Within the critical data level, there can be levels of more or less criticality. The accuracy levels will be determined by such criticality and dictate how many Snipers will review the Snip-It. If more than one Sniper, sniper results will be compared. If the results do not match, the Snip-It is sent to a third Sniper. If the results match with one of the previous two Sniper's results, the data is accepted. The Sniper that missed the translation is recorded in his/her accuracy ratings, and a less than acceptable accuracy rating could lose access for future work.

Form Page Template 520 as shown in FIG. 5 is created by using a blank or Clean Form 200 of the selected image form. The Clean Form 200 has areas 515 in 510 selected to identify positions in the form in which handwriting will be. These areas are preferably rectangular boxes 515. Each box 515 or a portion thereof, depending whether the handwritten data therein is deemed critical data vs. non-critical data, will be selected as handwritten data to be extracted for processing, a Snip-It. In an embodiment of the present method, an overlay of the pre-determined Form Page Template 520 over the selected form identifies precisely the fields of handwritten data to be extracted for processing. Again, these fields of image data or Snip-Its are catalogued based on criticality and delivered into the Snip-It management process. The Snip-It management process includes the management of the Snip-It, as shown in FIG. 7, the Snip-It Queue of FIG. 9, and the Snip-It processing shown in FIGS. 14A to 14D.

Figure 6:
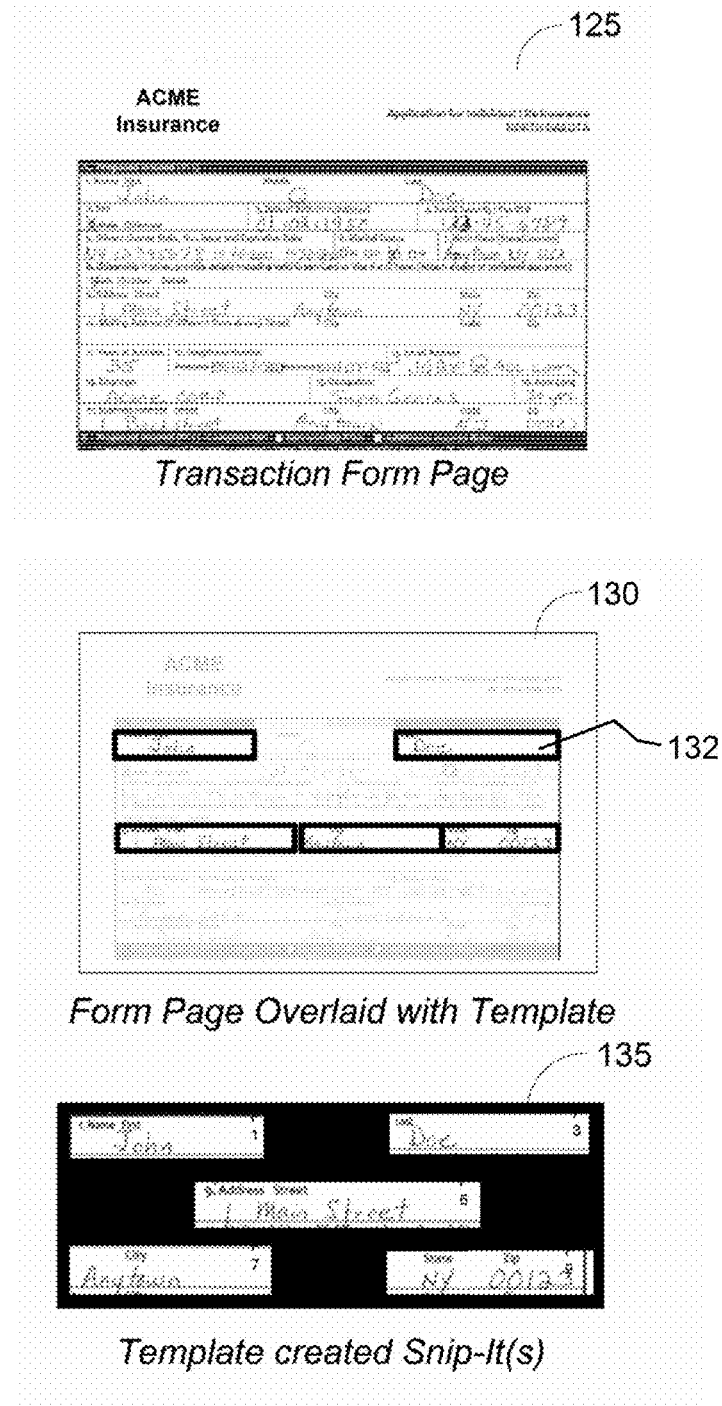
FIG. 6 illustrates the creation of a template created Snip-It in accordance with the present disclosure.

Referring to FIG. 6, the Transaction Form Page 125 identifies the Form Page Template 520 of FIG. 5 to overlay. The Form Page Template 520 overlaying the Transaction Form Page 125 identifies at 130 image fields 132 to be extracted for transcription and thus creates the Template created Snip-Its 135.

Figures 8, 9:
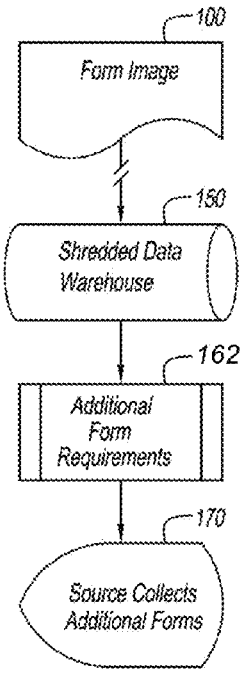
FIG. 8 represents a second round of the form and data collection in accordance with an embodiment of the present disclosure.
FIG. 9 is a schematic of the Snip-It Queue according to an embodiment of the present disclosure.

The Snip-It management process has a turn-around-time (TAT) shown in FIG. 9, that sets the queuing of each Snip-It in the data entry process. At the present time, as shown in FIG. 9, four TAT categories are defined as Real-Time, Expedite, Standard and Backfile. However, any number, more than two TAT, can be created. Again, each Snip-It will be classified for security noted above and, thus, the need for accuracy.

Accuracy is defined by how many times the Snip-It is keyed by a different number of Snipers, namely one, two or three Snipers. This accuracy is directly related to the security and/or critical nature of the Snip-It. Key fields, i.e. social security number, account number, and other such numerical data can be keyed two or more times (99.9% accuracy) where other informational fields can be keyed only once (98.0% accuracy). Accuracy can be further enhanced with third party validation integrations (i.e. LexisNexis, credit bureaus, government watch list, and the like).

Again, FIG. 7 illustrates another aspect the Snip-It management process 700 that allows for processing of NPI and PHI without context. Accordingly, this feature provides further security, even from Snipers. Currently, "blur" information is used on form pages so that the Sniper can only see data to key. This current conventional method may focus a data operator on data to be transcribed, but leaves context visible to the data operator. This exposes the NPI and PHI to data relationships that create a violation of NPI and PHI access. The method of the present disclosure extracts relevant image fields (Snip-It) from the forms removing context to the business transaction and queues the Snip-It in a manner whereby the Sniper never receives Snip-Its from the same form.

Figure 10:
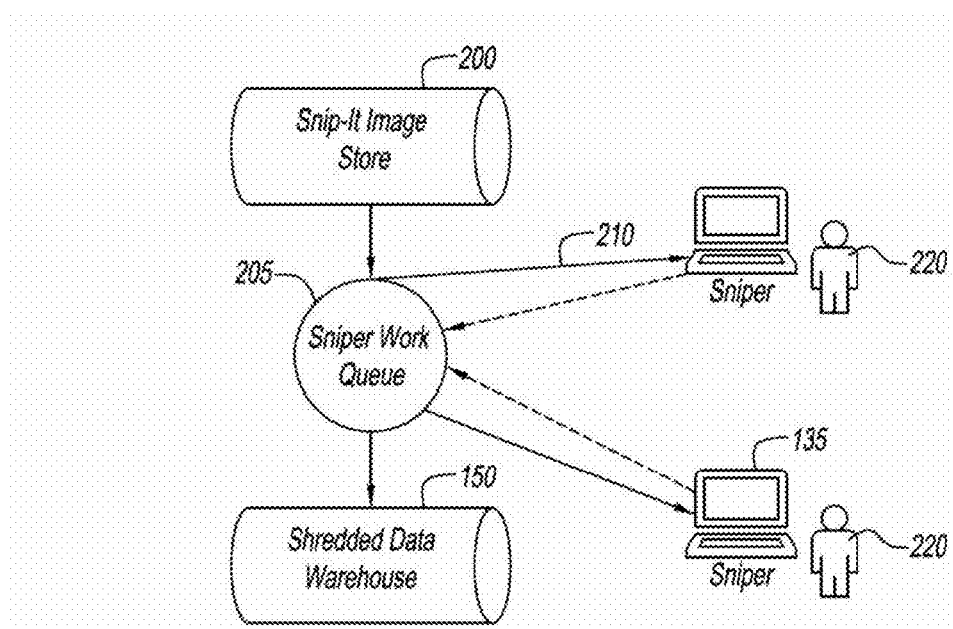
FIG. 10 illustrates processing a Snip-It to data according to the methods of the present disclosure.

Referring to FIG. 10, the method of the present disclosure delivers from the Snip-It image store 200, Snip-Its to a Sniper work queue 205. The work queue 205 delivers, and receives, Snip-Its over a secure virtual private network 210 connected to a plurality of Snipers 220. The secured network 210 has a secure application or Sandbox. Sandbox is defined as a special purpose browser application which isolates the browser from the physical computing system being used by a Sniper. This feature of the present methods ensures that common computing threats, such as viruses and malware programs, are isolated to protect the process from unauthorized access.

Once a Sniper 220 receives a Snip-It, the Snip-It will be processed within a defined period of time. As shown in FIG. 9, times 230 for each Snip-It and for each Sniper 220 is recorded. Significantly, if Sniper 220 does not transcribe the Snip-It in the defined period of time 230, the Snip-It will be removed and placed back into the queue for the next available Sniper.

The methods of the present disclosure envision other types of data operators or Snipers. For example, a special group of Snipers, called Forms Setup (FS) Snipers, will focus on working with the customers to setup their forms into the FST or templates and, possibly maintenance of those forms. The form process needed by a customer is simple. As discussed above during form recognition 120 and SFT 130, the process preferably includes two copies of the form pages, one clean and the other marked up reflecting Data Dictionary Terms. This FS Sniper configures the clean copy of the form page via the Snip-It application. Significantly, the FS Sniper is not involved in any Non Public Information (NPI). There is also a Form Rec (FR) Sniper. This FR Sniper is involved in form page recognition and quality control. A new customer form starts with the analysis of which document recognition method to use, pattern recognition, FR Sniper or both. FR Sniper is the preferred method when clear identifiable information is present on the form to identify a page 100%.

A transcribed Snip-It is called a Data-Snip. These data snips are returned to Shredded Data Warehouse 150 as shown in FIGS. 1 and 8. Once in Shredded Data Warehouse 150, the data-snips are stored into a data warehouse silo as displayed in FIG. 11 where the Snip-It ID shown in FIG. 12 comprises encoded information to include, but be not limited to, the transaction ID, which is a unique transaction ID assigned to every new transaction form that arrives for processing, Form/Page ID 208 of FIG. 2, the Data Dictionary/Term ID 400 of FIG. 4, and Snip-It location that is its position in FIGS. 6 and 7.

The Shredded Data Warehouse 150 of the present disclosure ensures privacy because there is no context to data fields, as in a traditional database organization. Traditional databases collect related fields and put them together in a row of information known as a record. Many records define a table and a collection of tables constitute a database. Shredded data offers no organization. Therefore, if there is an unauthorized access to NPI and PHI (e.g., hacking) data storage, the content stolen is meaningless. This avoids what has happened in the past, namely Anthem had a data breach on February 2015, since the hacker circumvented encryption via SQL injection and downloaded traditional database records.

Figure 13:
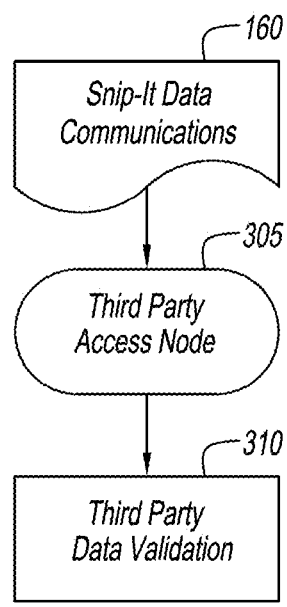
FIG. 13 illustrates a third party data access and validation process for a communication processed according to the present disclosure.

The Shredded Data Warehouse 150 will receive and store data from Snipers, and offers the most secure method to protect information from unauthorized access. Further, the Shredded Data Warehouse 150 offers the opportunity to do data validation with third party services (i.e. Lexis Nexis, Medical Information Bureau, CFPB, and the like), as shown at 310 in FIG. 13. [This FIG. 13 due to changes does not make sense] The Shredded Data Warehouse 150 provides Big Data, Data Collaboration, Many to Many Access, compliance and most of all, secure data.

Figure 12:
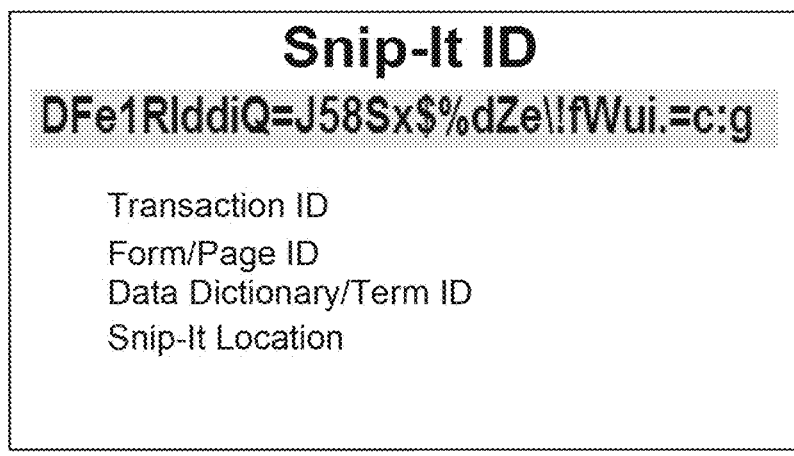
FIG. 12 illustrates a Snip-It ID according to the present disclosure.

Data-Snips are stored in the Shredded Data Warehouse 150 in a manner that pairs the data value with its unique Snip-It ID 610 shown in FIGS. 11 and 12. This pairing creates a Data-Snip. Data-Snips are stored in an SQL database as unique records. Each Data-Snip is identified by a unique Snip-It ID requiring several data elements that when encoded, creates from attributes (e.g., transaction ID, Form/Page ID, Data Dictionary/Term ID) and a Snip-It location. This Snip-It location or identification of its location then requires the processing of computer code to bring Data-Snips together with context (e.g. a row of data). The shredded data stored is, in effect, a group of what seems to be random data elements having no associations. Viewing the database table, like FIG. 11, would display numbers and/or characters that can be the beginning, middle or end of a social security number, birth date or address, credit card. Therefore, the data silo provides security since it cannot be viable information to one of unauthorized access, namely outside of the computing platform used to process the method described herein.

Referring to FIG. 8, after data has reached the Shredded Data Warehouse 150 and the Snip-It has been reassembled, based on transaction requirements/workflow it can be determined that there are additional form requirements 162 and a source to collect additional forms 170 since the initial processing cycle.

The methods of the present disclosure including the processing and storing data and documents optimizes the transcription, collection and storage of NPI and PHI information. The transaction company receives the benefit of IGO transactions before accepting documents and data into their computing infrastructure maximizing their process workflow and eliminates the introduction of NPI and PHI with no business purpose, only its liability.

NPI protection is designed to stop identity theft (i.e. credit card numbers, driver license, social security number, and the like). PHI is protected to stop discrimination based on health conditions. Some of this information by itself will produce unauthorized access to NPI therefore this information must be treated special so that the NPI is not disclosed. The present methods treat these data elements as a special category requiring special handling. These attributes (special data or not) are selected during setup when mapped to the Data Dictionary shown in FIG. 14A. Template setup, as shown in FIG. 14B, starts with the clean form/page and the marking of a rectangle box around the image area of interest. This will produce the X&Y coordinates on the form/page identifying the location of the Snip-It. As shown in FIG. 14B, the X coordinate measurement starts at points A/B that is zero point leading along the X-axis 0.63 inches to the upper left edge of the Snip-It and the Y axis starts that is the uppermost point of the Template Page. The upper left edge of the Snip-It starts along the X axis at 0.63 inches, and the Y-axis 1.63 inches down. The Snip-It ends at 3.63 inches along the X-axis and 2.25 inches along the Y- axis. Thus, the Snip-It location or location identifier is X0.63Y1.63-X3.63Y2.25 as shown in FIG. 14B. As also shown in FIG. 14B, the Snip-It location identification, shown in FIG. 12, can include more detail, besides the transaction number, Form ID, Form/Page ID, Data Dictionary, and Data Dictionary Term, such as whether there is Special Data, a Split Factor which is namely whether to split the Snip-It and, if so, how many times, and size of the data bit mask, as well as a date and time stamp for the date and time of entry. Of course, the coordinates/location of the Snip-It discussed above, are always in the Snip-It identification. As shown in FIG. 14A, using the Snip-It identification, the Snip-It is then mapped to a data dictionary term from the Data Dictionary 400 and, it is confirmed/determined whether the Snip-It requires special handling, namely the Special Data shown in FIG. 14B. Along with this attribute is the number of equal size segments 830 shown in FIG. 14D to split the Snip-It into (e.g., 0, 2, 3 or 4) for queuing to Snipers. Again, a sniper will only process the segment, not the entire field.

Figure 14C:
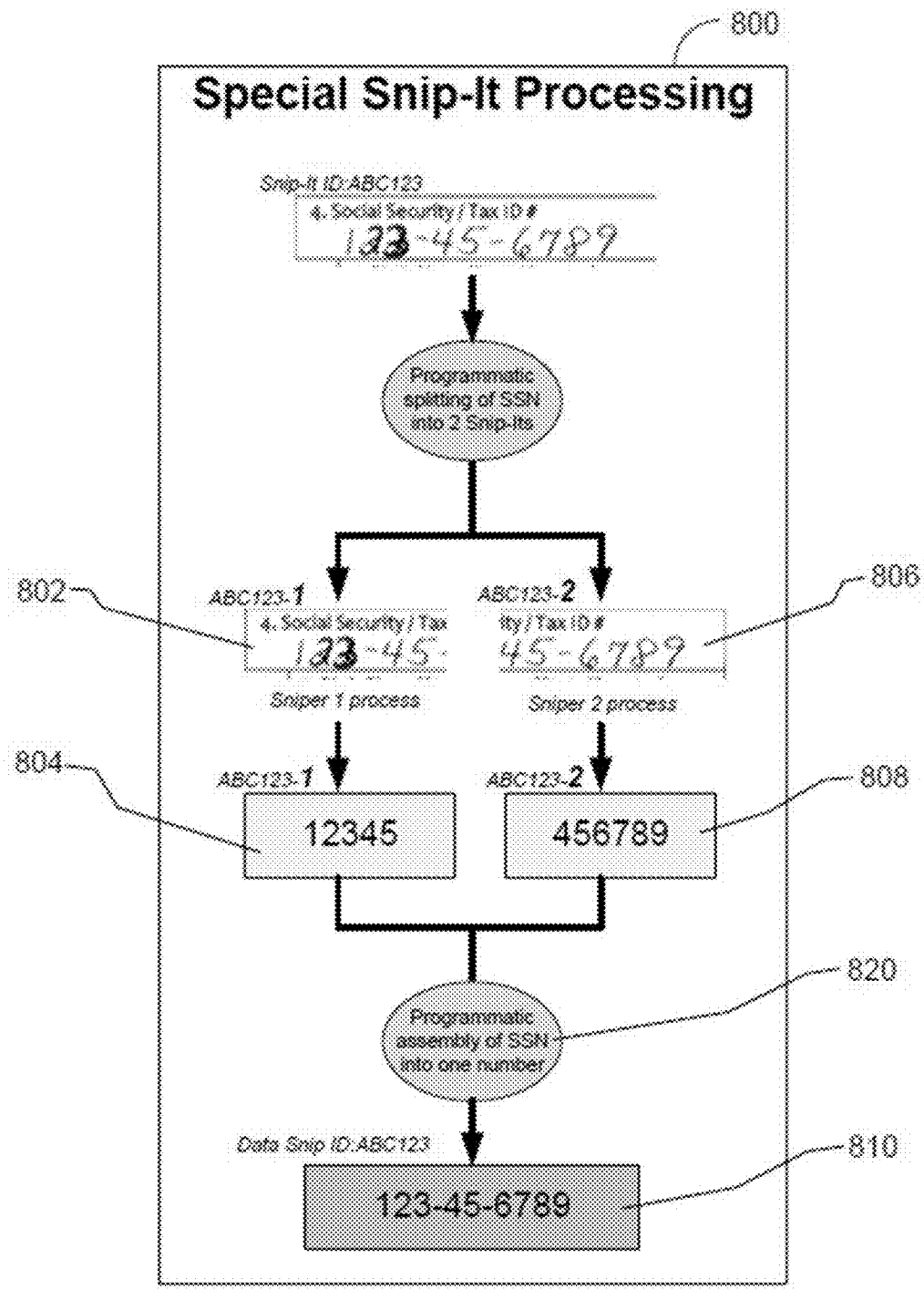
Figure 14D:
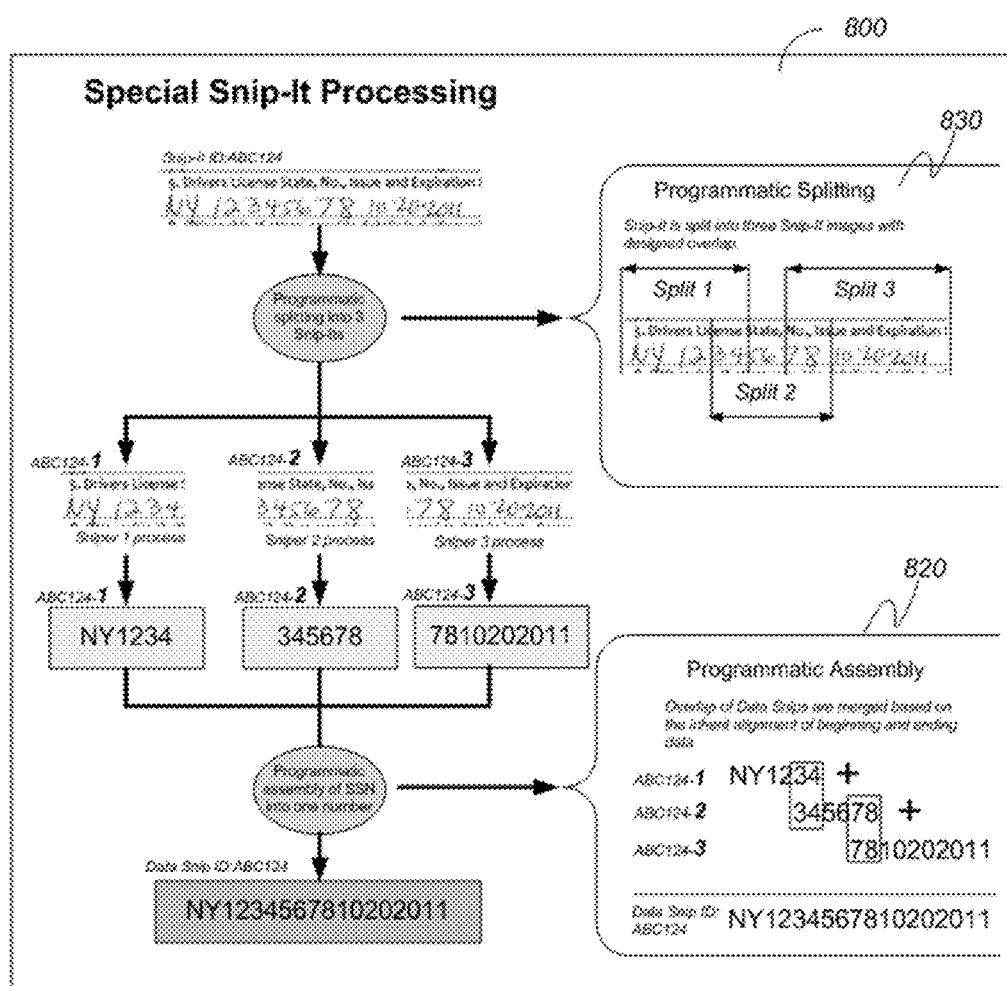

These special Snip-Its, once identified and returned as shown at 140 of FIG. 1, will be re-assembled via the Snip-It operations 820 shown in FIGS. 14C and 14D. Programmatic Assembly shown as 820 in FIG. 14D, is based on the string mask as defined in the Form Page Template. The required portion of the data entered by the Sniper is extracted then applied together with the other required portions, as defined in the Form Page Template, to create a valid social security number (SSN). If only two Snip-Its, such as the social security number shown in FIG. 14C, the print data 804 of Snip-It 802 and the print data 808 of Snip-It 806 merge towards each other to file the nine (9) character field of 810. Thus, the number "45" in the middle, that is duplicative in printed data 804 and 808, and will be scrubbed to one entry due to the nine (9) character field size. Again, security is maintained because Snipers will not have access to a complete special Snip-It field or in this case, SSN. Snip-It segments are designed to have overlap so when converted into data the data will have overlap.

For all Snip-Its, and especially where three or more Snip-Its are reassembled or placed back into context ("re-contexted"), knowing the field mask (e.g. how many total characters, numbers or letters and positions, Example—SSN ###-##-###) is important so that the returned data can determine the beginning and end of each segment and, therefore, how to merge or reassemble into one value.

In FIG. 14D, the special field being processed is a state driver license with a factor of three (3) or three segment processing. Segment 1 (NY1234) and segment 2 (345678) overlap on data value 34. Thirty four marks the end of segment 1 and 34 marks the beginning of segment 2. Therefore, 34 is used once to create NY12345678, not NY1234345678. The same process is applied to merging segment 2 with segment 3 where 78 is the end and beginning. Again, Snipers will never receive two special Snip-Its from the same form page. This splitting up of a form page into different Snip-Its and distributing the Snip-It to different Snipers maintains compliance since there is no context to the Snip-It. A Snip-It without context is just data elements with no value and protects NPI and PHI.

Again, Snipers will never receive two special Snip-Its from the same form page. This slicing up of a form page into different Snip-Its and distributing the Snip-It to Snipers maintains compliance since there is no context to the Snip-It. A Snip-It without context is just data elements with no value and protects NPI and PHI.

These methods of the present disclosure are not limited to NPI or PHI, but to any process where the transacting trading partners need to collaborate and be assured their information has the highest level of protection. Documents are management for originality, data is captured by the data entry method of choice, and data is stored in a manner in which it has no value to unauthorized access. Therefore, the benefits include the most secure way a community of organizations or trading partners can create and exchange information in a business transaction.

Also, fingerprinting imaged documents provide for subsequent programmatic interrogation of originality. Dispersing Snip-Its of image fields to different Snipers eliminates the unauthorized use of NPI and PHI. Storing captured data in a Shredded Data Warehouse 150 eliminates a hacker's ability to gain access to NPI and PHIs. Even a successful data breach, the hacker only views at a pile of shredded data elements that have no context. Interacting with the data silo via access-node 305 thwarts a man in the middle attacks.

The present methods provide a solution that is the combination of crowd sourcing and unique imaging technology. Crowd sourcing (CS) is limited to rapidly process an image Snip-It into data. It has been found that this process can deliver handwriting recognition with 99% accuracy and within seconds.

This method provides the best opportunity to protect an individual from identity thief and reduces the opportunity, liability and expense of data breaches. Transaction companies can reduce information technology cost by eliminating point to point custom development and ongoing maintenance cost, as well as decrease workflow cycle times.

The customer minimizes the time and resources required to achieve production operations. Receiving documents and data is a matter of weeks, not months or years. In many instances, customers can leverage existing document and data import formats (i.e. XML, Paired Values, CSV, and the like) thereby eliminating the need for IT development resources. Customers can control what information is time sensitive. For example, a customer may want an annuity application to process faster than a life term application. Accuracy levels will provide the customer a level of confidence in the data depending on the critical nature of the data. Also, a customer can follow their processing statistics via a web portal and receive alerts when various processing conditions arise.

In order to deliver the documents and data 160, this method will provide tokens to the transaction company or customer that will allow documents along with their data as collected and stored in the data silo to be delivered in proper context. Encoded into each token is reference to the original transaction ID. Based on the transaction ID, all Snip-It IDs can be constructed for each form page processed thereby reassembling the data back into context. The communication or transport of the documents, data and tokens can be accomplished in one or all of the following ways. A secure document exchange delivery can include a package of data that contains the documents, data and tokens. A secure web service API can allow for a programmed interface to receive the documents, data and tokens. A secure FTP (file transfer protocol) can deliver documents, data and tokens. A secure email delivery of a package of data can contain the documents, data and tokens. All of these methods would use industry standard technologies, such as XML, WSDL, SOAP, JSON, HTTP, SMTP and FTP.

The techniques described herein are exemplary, and should not be construed as implying any particular limitation on the present disclosure. It should be understood that various alternatives, combinations and modifications could be devised by those skilled in the art from the present disclosure. For example, steps associated with the processes or methods described herein can be performed in any order, unless otherwise specified or dictated by the steps themselves. The present disclosure is intended to embrace all such alternatives, modifications and variances that fall within the scope of the appended claims.

We claim:

1. A method for processing non-public, personal health information having handwritten data, the method includes the steps of:
   creating a template based on one or more data fields each having a plurality of handwritten data bits in a form that is selected based on a transaction company business requirements;
   mapping to a data dictionary library that defines industry standards of the business of the transaction company to assure all information requirements are met in the template; and
   sending, based on the template, a selected handwritten data bit from the plurality of data bits to one of a plurality of data operators to determine the handwritten data bit and provide a print form of same within seconds of receipt by the data operator.

2. The method of claim 1, further comprising identifiers of coordinates of a position of each of the plurality of handwritten data fields in the template.

3. The method of claim 1, further comprising a data bit management system for managing each of the plurality of handwritten data bits and the sending of each of the plurality of handwritten data bits to a different one of the plurality of data operators.

4. The method of claim 3, wherein the data bit management system establishes criticality of each handwritten data bit in the plurality of handwritten data bits.

5. The method of claim 4, wherein the established criticality determines the number of discrete handwritten data bits from the plurality of handwritten data bits in each of the one or more data fields.

6. The method of claim 3, wherein the data bit management system manages the sequencing of the plurality of the handwritten data bits to the plurality of data operators.

7. The method of claim 3, wherein the data bit management system monitors a response time for each of the plurality of data operators.

8. The method of claim 7, wherein the response time is the time from which a handwritten data bit is received by the data operator to the time the data operator returns a converted printed data bit to the data bit management system.

9. The method of claim 1, further comprising selected assembly of printed data bits into context for distribution of a document.

10. The method of claim 1, further comprising providing an identifier on the handwritten data bits that can only be placed into context with appropriate instructional information.

11. The method of claim 1, further comprising storing the handwritten data bits in an out of context format to provide security.

12. The method of claim 1, further comprising storing the plurality of data bits in a selected warehouse so that no personal information can be determined until the information is placed into context even if unauthorized access occurs.

13. The method of claim 1, further comprising collecting an initial transaction document having one or more form images and assigning a transaction ID to the document and a unique identifier to each image form; and performing a form recognition step to completely identify the document and the form images using bit map pattern analysis and programmatic matching of any unidentified form images of a document to a pre-configured form of the transaction company stored in a library, to assist in the creating of the template.

14. The method of claim 1, wherein creation of the template includes using a clean image form and marking of a rectangle box around an image area of interest to produce X and Y coordinates of the image area.

15. The method of claim 1, wherein each of the plurality of handwritten data bits has a location identification that includes coordinates of the handwritten data bit.

16. The method of claim 15, wherein the location identification also includes a transaction number, an image form and document identification, and a data dictionary term.

17. The method of claim 16, wherein the location identification further includes a special data designation, a split factor that instructs how many times a handwritten data bit should be split into different data bits.

18. A method for processing non-public, personal health information having handwritten data, the method includes the steps of:
  creating a template based on one or more data fields each having a plurality of handwritten data bits in a form that is selected based on a transaction company business requirements and identifying a precise position of each of the plurality of handwritten data fields in each of the one or more data fields;
  mapping to a data dictionary library that defines industry standards of the business of the transaction company to assure all information requirements are met in the template;
  sending, from a data bit management system, a selected handwritten data bit from the plurality of handwritten data bits in each of the one or more data fields to one of a plurality of data operators to translate the handwritten data bit into a print form, wherein the one of the plurality of operators returns the print form to the data bit management system within seconds of receipt by the one data operator; and
  selected assembling of print forms into context for distribution of a document.

19. The method of claim 18, wherein the plurality of handwritten data bits are stored in a warehouse and out of context to preserve the security of each of the plurality of handwritten data.

* * * * *